(12) United States Patent
Tovar et al.

(10) Patent No.: US 7,447,340 B2
(45) Date of Patent: Nov. 4, 2008

(54) DEVICE AND METHOD FOR AUTOMATICALLY PRODUCING A THERMAL RECOIL RESPONSE IN NEMATODES

(75) Inventors: Karlheinz Tovar, Erbes-Büdesheim (DE); Gerhard Weidner, Utting (DE); Evelyn Braungart, München (DE)

(73) Assignee: NemaGain Research, LLC, Black Earth, WI (US)

( * ) Notice: Subject to any disclaimer, the term of this patent is extended or adjusted under 35 U.S.C. 154(b) by 1050 days.

(21) Appl. No.: 10/472,264

(22) PCT Filed: Mar. 18, 2002

(86) PCT No.: PCT/EP02/02976

§ 371 (c)(1),
(2), (4) Date: Apr. 30, 2004

(87) PCT Pub. No.: WO02/075293

PCT Pub. Date: Sep. 26, 2002

(65) Prior Publication Data

US 2004/0234451 A1 Nov. 25, 2004

(30) Foreign Application Priority Data

Mar. 16, 2001 (DE) ................................ 101 12 798

(51) Int. Cl.
*G06K 9/00* (2006.01)
*A61K 51/00* (2006.01)

(52) U.S. Cl. ...................... 382/128; 424/9.2; 382/133; 435/286.1; 435/808; 435/288.7; 435/29; 435/30; 356/36; 356/38; 356/338; 356/341; 356/343

(58) Field of Classification Search ............... 382/128, 382/133; 435/286.1, 808, 288.7, 29, 30, 435/34; 356/36, 38, 337, 338, 341, 343; 250/458.1–462.1; 424/9.2; 607/84
See application file for complete search history.

(56) References Cited

U.S. PATENT DOCUMENTS 5,480,804 A * 1/1996 Niwa et al. ............... 435/286.1

(Continued)

FOREIGN PATENT DOCUMENTS

DE 0935132 * 2/1999

(Continued)

OTHER PUBLICATIONS

Distribution and movement of *Caenorhabditis elegans* on a thermal gradient, Yamada et al, May 2003.*

(Continued)

*Primary Examiner*—Andrew W. Johns
*Assistant Examiner*—Nancy Bitar
(74) *Attorney, Agent, or Firm*—Lahive & Cockfield, LLP; Elizabeth A. Hanley, Esq

(57) ABSTRACT

The invention relates to a device (10) and a method for automatically eliciting a thermal avoidance response in nematodes, particularly in order to test pharmaceutical substances. The device (10) has a bearing surface (12) on which sample containers (14) of nematodes (16) are disposed, a laser (18), a selective laser-beam interrupter (27) to regulate the length of the laser pulse, aft and a scanner (22) for projecting and focussing the laser beam and for controlling a deflection. A light source (28) illuminates the sample container (14) with light, which brings about a contrast in the nematodes in the container. An additional light source (29) can also illuminate the sample container (14) with light in order to excite fluorescence-labeled areas of the nematodes, causing them to fluoresce. A real-time image processing device connected to the camera (30) determines the respective positions of all areas relevant for laser irradiation of the nematodes and makes this information available to a controller (32). The beam path of laser (18) is directed sequentially to different areas of individual nematodes by the controller using the scanner (22).

24 Claims, 1 Drawing Sheet

U.S. PATENT DOCUMENTS

| | | | |
|---|---|---|---|
| 6,444,665 B1 * | 9/2002 | Helton et al. | 514/220 |
| 6,702,996 B1 * | 3/2004 | Baumeister et al. | 424/9.2 |
| 6,995,841 B2 * | 2/2006 | Scott et al. | 356/318 |
| 2005/0062837 A1 * | 3/2005 | Kim | 347/233 |
| 2007/0111027 A1 * | 5/2007 | Chen et al. | 428/690 |

FOREIGN PATENT DOCUMENTS

| | | |
|---|---|---|
| DE | 199 24 929 C2 | 12/2000 |
| EP | 0 935 132 A2 | 8/1999 |
| GB | 2231958 * | 11/1990 |
| GB | 2231958 A | 11/1990 |
| JP | 0284660 * | 8/1997 |

OTHER PUBLICATIONS

Thermal avoidance in *Caenorhabditis elegan*: An approach to the study of npciception, Aug. 1999.*

* cited by examiner

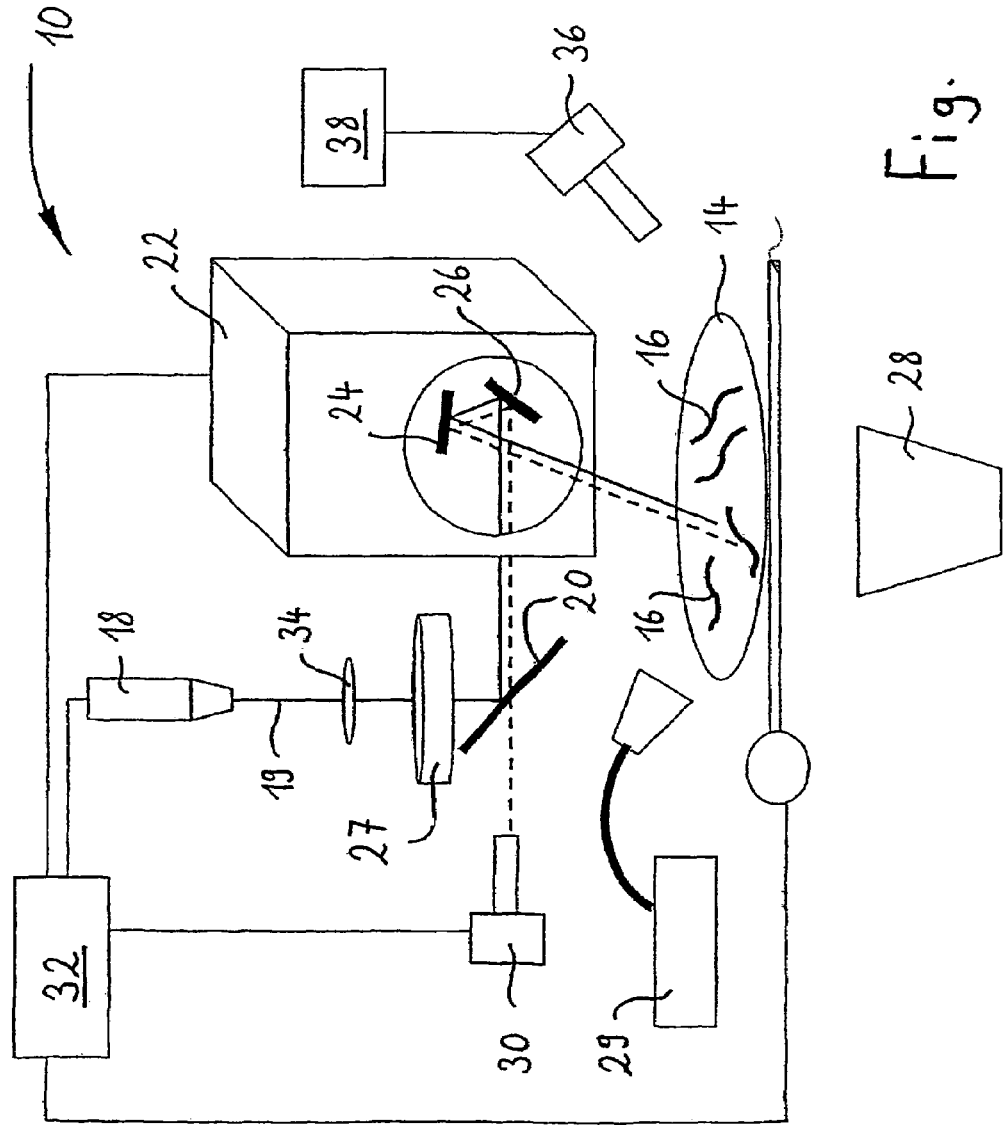

DEVICE AND METHOD FOR AUTOMATICALLY PRODUCING A THERMAL RECOIL RESPONSE IN NEMATODES

The present invention relates to a device and method for automatically eliciting a thermal avoidance response in nematodes.

DE 199 24 929 A1, for example, teaches that certain lower organisms, particularly nematodes (roundworms), are suitable for testing the action of pharmacologic substances, particularly algogenic and analgesic substances. The interesting point in this connection is that the results of such tests performed on nematodes have relatively good transferability to higher organisms, particularly humans. When such tests are carried out, a heat stimulus is applied to the nematodes that leads to a withdrawal reflex in the nematode. If the nematodes have been exposed to an investigational pharmacologically active substance, their thermal avoidance response differs from the normal reflex behavior of such nematodes not exposed to the investigational substance. In other words, the thermal avoidance response of a nematode in response to a heat stimulus is predictive of whether or not a pharmacological substance to be tested has a desired effect. Normally, nematodes of the genus *Caenorhabditis*, particularly *Caenorhabditis elegans* and mutants thereof, are used for these investigations.

For rapid, economical performance of such investigations, an automated device and an automated method for producing a thermal avoidance response are needed. The goal of the invention is to provide such a device and such a method.

This goal is achieved according to the invention with a device having the features stated in claim 1. According to what is stated there, it comprises a bearing surface for supporting one or more sample containers in which the nematodes to be investigated are placed. It has been established that the tail region and more particularly the head region of nematodes respond with particular sensitivity to a heat stimulus, for which reason in the device according to the invention the tail region and/or head region of the nematodes to be investigated is/are preferably exposed to a well-defined heat stimulus. In one embodiment, the head region and/or the tail region of the nematodes to be investigated is/are labeled with a fluorescent dye.

The device according to the invention additionally comprises a laser, preferably a laser emitting infrared light, to generate the heat stimulus to be applied to the nematodes; a selective laser-beam interrupter to regulate the length of the laser pulse; and a scanner located in the beam path of the laser and serving to project and focus the emitted laser beam on at least the region of one sample container on the bearing surface and to deflect the emitted laser beam in a controlled manner within this region. A light source is also present, preferably consisting of a red diode array that illuminates in reflection or transmission at least the sample container (which may be transparent), which brings about contrast in the nematodes located in the container. Light sources differing in wavelength can be used for both reflection and transmission illumination. The light source may for example be a cold light source that radiates light of a given wavelength, which excites for example fluorescence-labeled regions of the nematodes being investigated to fluoresce.

A beam splitter located in the beam path of the laser separates the emitted laser light from the light used for contrasting the nematodes or for fluorescence labeling of certain nematode regions. By means of an electronic camera cooperating with this beam splitter and sensitive to the light used for contrasting the nematodes or for fluorescence labeling of certain nematode regions, and by means of a real-time image-processing device that is connected to the electronic camera and determines the respective positions of all the nematodes in the sample container, the device according to the invention continuously determines where the nematodes are located. Based on this information, a controller connected to the image-processing device, to the laser, to the selective laser-beam interrupter, and to the scanner, points the laser beam path with the aid of the scanner at a number of nematodes located in the container, one after another, and causes the selective laser-beam interrupter to emit a laser beam every time the laser beam path has been directed at one nematode. In this way, a stimulus can automatically be applied to all the nematodes in the container, and thus for example to all the nematode heads.

If the laser is an infrared-emitting laser, the beam splitter is preferably opaque to the emitted laser light and transparent to the light used for contrasting the nematodes or fluorescence labeling of certain nematode regions. Here, the electronic camera is preferably located behind the beam splitter (relative to the beam direction of the light coming from the nematodes).

In a preferred embodiment of the device according to the invention, the laser is an Nd:YAG laser with a wavelength of 1064 nm. Lasers with another wavelength can also be used, in which case the beam splitter in the beam path of the laser may have to be adapted. Depending on the wavelength of the laser light used, it could be more advantageous to have a beam splitter that is transparent to the emitted laser light and reflects the light used for contrasting the nematodes or for fluorescence labeling of certain nematode regions out from the beam path of the laser to the electronic camera.

Regardless of the type of laser used, in certain embodiments of the device according to the invention a filter is disposed between the beam splitter and the electronic camera. In one embodiment, in which certain nematode regions are preferably labeled with a fluorescent dye, the filter used is one that is preferably transparent to the light emitted by the fluorescence-labeled regions of the nematodes, in particular to light with a wavelength of 509 nm. This wavelength corresponds to the fluorescent light emitted by the nematodes. The filter thus ensures that no (interfering) light differing in wavelength, particularly the light used to excite fluorescence, is sensed by the electronic camera.

Preferably, the laser used is operated continuously and its power is continuously adjustable so that the intensity of the heat stimulus to be applied can be adapted to various conditions. Lasers with a maximum output power of 50 mW to 1000 mW for example are suitable.

In the investigated container, which may be transparent, the illuminated area should have a diameter in the range of approximately 50 µm to approximately 200 µm and has, in a preferred embodiment of the device according to the invention, a diameter of 150 µm. Depending on the laser, scanner and scanner objective used, it may be necessary to dispose a beam expander in the beam path of the laser in order to produce a laser spot of the desired diameter, 150 µm for example, in the container.

To regulate the time during which the laser beam acts on the target (pulse length), a shutter is located in particular between a continuously operated laser and the beam splitter. A shutter is an electromechanical device located in the beam path of a laser. This device enables the beam path of the laser to be interrupted or opened selectively for a well-defined period of time and thus, with a continuously operated laser, enables the pulse length of the laser beam to be regulated. The shutter is connected to a controller through which the shutter receives an electrical signal that causes an electromechanically actuated obstacle in the beam path of the laser to be opened or closed. Preferably, the shutter is connected via the controller to an image-processing program. The opening time of the shutter is continuously adjustable and, in a preferred embodiment of the device according to the invention, lasts 0.01 to 3 seconds, preferably 0.3 to 1 second.

The scanner is preferably a so-called galvanometer scanner with movable scan mirrors and an objective known as an f-theta objective.

To increase the degree of automation of the device according to the invention, the bearing surface on which the container or containers to be investigated are located is preferably in the form of a motorized stage that can be moved at least in the x and y directions, and can also be moved in the z direction for focussing the object plane. Such a motorized stage can be coupled with the above-mentioned controller so that once all the nematodes in a container have been "shot" with laser light, the motorized stage can be automatically moved to position the next container under the region of the device covered by the scanner.

The image-processing device of the device according to the invention is preferably designed such that it continuously calculates the contour and/or the midpoint and/or at least one end point of each of the nematodes located in the container. In another embodiment, the (areal) center of gravity of each of the fluorescence-labeled regions of the individual nematodes in the container currently being examined is calculated. If desired, the areal center of gravity of the pictured nematode can also be calculated from the contour of the object. The coordinates of the object contours and/or midpoints and/or end points and/or areal centers of gravity determined are continuously transmitted to the controller, preferably as vector coordinates, and can moreover be documented to facilitate subsequent evaluation of the test results.

According to a preferred further embodiment of the device according to the invention, another camera is present that is sensitive to the infrared light emitted by the laser and continuously takes images of the container currently being examined, which can also be documented. By means of this additional camera, a determination can be made as to whether or not the emitted laser beam has actually hit the target region, possibly fluorescence-labeled, of a nematode. Moreover, the thermal avoidance responses of the nematodes can be monitored with this additional camera. If the images taken by this additional camera are documented, one can determine whether or not an experiment has run properly even after the experiment is complete.

To ensure consistent experimental conditions, the device according to the invention is in an environment in which the temperature is set to a constant temperature in the range of 10° C. to 30° C., preferably to 15° C. to 25° C., for example by means of a heating and cooling device. The relative humidity of the environment is set, with a humidifier for example, to a value of 40% to 70%, preferably to 50% to 60%.

The goal of the invention referred to at the outset is also achieved by a method for automatically eliciting a thermal avoidance response in nematodes, that comprises the steps listed in claim 19. In one embodiment, the body contours of the nematodes are determined by an edge detection method. Based on the information thus obtained for the object contour, the center of gravity and/or at least one end point is/are calculated and the position coordinates of these points, specific to an object, are determined. By comparing the change in the position coordinates in successive camera images, the position of the head of the predominantly forward-moving nematodes can be determined. In another embodiment, those pixels from the camera image that lie within certain color-value or grey-scale-value threshold values are first defined as components of relevant objects. The threshold values are calibrated such that they optimally take into account the way in which the nematodes are optically reproduced. In the next step, contiguous pixels that lie within certain size threshold values are defined as relevant objects. In a further step, the resulting objects are reduced by a skeletonizing method to a one-pixel-wide line. In the next step, from the individual lines their midpoint and/or at least one end point is/are determined and the position coordinates of these points specific to an object are determined. By comparing the change in the position coordinates in successive camera images, the positions of the heads of the predominantly forward-moving nematodes can be determined. In another embodiment, fluorescencing regions of the nematodes are observed continuously by an electronic camera, the areal center of gravity of each fluorescence-labeled region is continuously calculated, and the resulting center-of-gravity coordinates are transmitted to a controller of a scanner.

Based on the coordinates delivered to the controller, a laser beam, preferably an infrared laser beam, is led by means of the scanner to a first selected head or tail region of a nematode, then to a second nematode, then to a third nematode, and so forth until all the nematodes in a unit for examination, for example a container, have been processed.

According to one preferred embodiment of the method according to the invention, first only the beam path of the infrared laser beam is pointed at the first selected nematode and the (infrared) laser beam—triggered by the controller—is not sent out until the beam path of the laser beam has been pointed at the head or tail region of a selected nematode. In this way, the laser is used only when actually needed to produce a heat stimulus.

To facilitate image processing and always ensure correct assignment of the calculated coordinates for object contours, end points, midpoints and areal centers of gravity, the beam path of the laser beam is preferably pointed at a reference position before each pointing at a nematode region. Starting from this reference position, it is steered to the selected nematode. According to another embodiment, the beam path of the laser beam is first pointed at a reference position and then at several selected nematodes one after the other. In either case the reference position can be for example the image center of the image field observed by the electronic camera.

Although an infrared laser is preferably used for the device according to the invention and the method according to the invention, in theory any laser that makes it possible to produce a heat stimulus evoking a thermal avoidance response in the nematodes under examination is suitable.

A preferred sample embodiment of a device according to the invention will now be described in greater detail with reference to the accompanying single FIGURE.

The FIGURE shows a device designated overall as "10" for automatically producing a thermal avoidance response in nematodes. Device 10 has a bearing surface 12 to support several containers 14, only one of which is shown in the FIGURE. In the example illustrated, bearing surface 12 is in the form of a motorized stage that can be moved in the x, y, and z directions.

The container 14, which can for example be an agar dish, contains the nematodes 16 under examination, usually about 5 to 15 nematodes per container (in the FIGURE only four nematodes 16 are shown). The region of interest of each one of these nematodes, for example the highly heat-sensitive head region, can be labeled with a fluorescent dye.

A laser 18, which in the present example is a diode pumped Nd:YAG solid state laser with a wavelength of 1064 nm and a maximum output power of 300 mW, is used to produce a heat stimulus necessary to evoke a thermal avoidance response by the nematodes. The output power of continuously operated laser 18 is continuously adjustable between 0 and 100%. The infrared laser beam 19 emitted by laser 18 is then sent via a beam splitter 20 to a galvanometer scanner 22 with movable silver-coated scan mirrors 24, 26 when a shutter 27 located between the laser and the beam splitter is open. The opening time per laser pulse is continuously adjustable between 0.01 second and 3 seconds. The scan mirrors 24, 26 can direct the emitted laser beam 19, represented in the FIGURE by a solid line, to a desired location in container 14.

A light source 28, here in the form of a red diode array, illuminates in transmission the container 14 to be examined, which brings about a contrast in the nematodes contained therein. Additionally, a light source 29, here in the form of a cold light source with a wavelength of 480 nm, can illuminate in transmission the container for examination, and this light excites the fluorescence-labeled regions of the nematodes in the container to fluoresce. In the present example, the fluorescence-labeled regions of the nematodes so illuminated fluoresce at a wavelength of 509 nm.

The light proceeding from the object plane in which nematodes 16 are located, represented in the FIGURE by a dashed line, is reflected by scan mirrors 24, 26 to beam splitter 20, which is transparent to light with this wavelength but opaque to the infrared light emitted by laser 18. An electronic camera 30 disposed behind beam splitter 20 relative to the direction of the emitted light, in this case a CMOS camera, is sensitive to this light. A filter not shown in the FIGURE is disposed between the electronic camera 30 and the beam splitter 20, said filter being transparent to the light emitted by the fluorescence-labeled regions of the nematodes 16. In the present example, the filter is a long pass filter, opaque to light with a wavelength less than 509 nm. Because of this, camera 30 sees only the fluorescence-labeled regions of nematodes 16 and not the light used to excite fluorescence.

The image taken continuously by camera 30 is fed to a real-time image processing device which is integrated into a controller 32 and connected thereto. The image processing device continuously determines the current positions of all the nematodes based on the images it receives, and at the same time calculates the object contour and/or the midpoint and/or at least one of the end points and/or the center of gravity of the individual objects detected. The coordinates of all the calculated object contours, centers of gravity, midpoints, or end points are conveyed to controller 32 as vector coordinates.

The controller 32, which furthermore is connected to laser 18, shutter 27, and scanner 22, can thus, based on the data available to it, point the beam path of laser 18 at various nematodes in the container 14 one after the other by correspondingly moving scan mirrors 24, 26. Whenever the beam path of laser 18 has been pointed at a selected nematode, controller 32 sends a signal to shutter 27, which then emits a laser beam that triggers a heat stimulus when it hits the target region of a nematode 16. In this manner, all the nematodes in container 14 are "shot" with laser light one after another. Before each "shot," the beam path of laser 18 moves to a reference position, which in the example described is the center of the image of the image field observed by electronic camera 30.

Once all the nematodes in a container 14 have been shot with laser light, the controller 32 operates the motorized stage serving as bearing surface 12 such that it moves another container into the scanning position. The individual containers can for example be present in a row or in several rows arranged in sequence.

In order for a sufficiently large laser light spot to be produced in the container 14 examined—in the example described this laser light spot has a diameter of 150 μm—it may be necessary to provide a beam expander 34 in the beam path of laser 18.

So that the result of the laser light shot can be monitored, i.e. for improved determination of whether the laser beam has actually hit the target region of a nematode, and has then led to a thermal avoidance response, device 10 has has an additional camera 36 that is sensitive to the infrared light emitted by laser 18 and is preferably also an electronic CMOS camera. This camera 37 continuously observes the region of the container 14 currently being examined and stores the images taken thereby in a documentation device 38, which is for example a computer hard disk, a video recorder, or a DVD recorder.

The invention claimed is:

1. A device (10) for automatically eliciting a thermal avoidance response in nematodes, comprising:
    a bearing surface (12) for supporting one or more sample containers (14) that serve to accept the nematodes (16) to be investigated,
    a laser (18),
    a selective laser-beam interrupter,
    a scanner (22) disposed in a beam path of the laser for projecting and focussing an emitted laser beam (19) onto at least a region of a sample container (14) in contact with the bearing surface (12) and for controlled deflection of the emitted laser beam (19) in said region,
    a laser source (28) that illuminates the sample container (14) to be investigated with light, the light effecting a contrast in the nematodes located in the container,
    a light source (29) that illuminates the container (14) to be investigated with light that excites fluorescence-labeled regions of the nematode to emit fluorescent light,
    a beam splitter (20) in the beam path of laser (18), which separates the emitted laser beam from one of the light used for contrasting the nematodes and the fluorescent light emitted by the fluorescence-labeled regions of the nematodes,
    an electronic camera (30) cooperating with the beam splitter (20) and sensitive to light emitted from the nematodes,
    a real-time image processing device connected with the electronic camera (30) that determines a current position for each of the nematodes, and
    a controller (32) connected to the laser (18), the selective laser-beam interrupter, and the scanner (22), wherein the controller, by means of the scanner (22), directs the beam path of the laser (18) at various nematodes one after another and controls the selective laser-beam interrupter to emit a laser beam when the laser beam path points at a relevant region of each nematode for a laser shot.

2. A device according to claim 1, characterized in that the laser (18) is an infrared laser, that the beam splitter (20) is opaque to the emitted laser light and is transparent to light emitted from the nematodes, and that the electronic camera (30) is disposed behind beam splitter (20).

3. A device according to claim 2, characterized in that the laser (18) is an Nd:YAG laser with a wavelength of 1064 nm.

4. A device according to claim 1, characterized in that between beam splitter (20) and electronic camera (30), a filter is located that is opaque to the light that excites the fluorescence-labeled regions of the nematodes to emit fluorescent light and is transparent to the light emitted by the fluorescence-labeled regions of the nematodes.

5. A device according to claim 1, characterized in that the emitted power of the laser (18) is continuously adjustable.

6. A device according to claim 1, characterized in that the selective laser-beam interrupter is a shutter (27) disposed in the beam path of laser (18).

7. device according to claim 6, characterized in that the opening time of the shutter (27) is continuously adjustable.

8. A device according to claim 1, characterized in that a beam expander (34) is disposed in the beam path of laser (18).

9. A device according to claim 1, characterized in that the scanner (22) is a galvanometer scanner.

10. A device according to claim 1, characterized in that the bearing surface (12) is a motorized stage movable at least in the x and y directions and preferably in the z direction and is coupled to the controller (32).

11. A device according to claim 10, characterized in that, by means of the motorized stage, the controller (32) moves another container (14) of said one or more sample containers into the region of bearing surface (12) illuminated by laser (18) after processing the nematodes in the first container (14).

12. A device according to claim 1, characterized in that the image processing device continuously calculates at least one of the midpoint and at least one end point of a plurality of nematodes present in the container (14).

13. A device according to claim 1, characterized in that the image processing device continuously calculates the object contour of each of the nematodes present in the container (14).

14. A device according to claim 1, characterized in that the image processing device continuously calculates the center of gravity of each of the fluorescence-labeled regions in the container (14) currently being examined.

15. A device according to claim 1, characterized in that the image processing device documents the calculated object contours the midpoints, the end points and the centers of gravity of each of the nematodes present in the container (14).

16. A device according to claim 1, characterized in that an additional camera (36) is present that is sensitive to the infrared light emitted by laser (18) and continuously takes images of the container (14).

17. A device according to claim 16, characterized in that the images taken by additional camera (36) are documented.

18. A device according to claim 1, further comprising a device for keeping the temperature and relative humidity of the environment of the device for automatically eliciting a thermal avoidance response in nematodes constant.

19. A method for automatically eliciting a thermal avoidance response in nematodes or similar organisms, comprising the steps of:
    observing one of nematodes located in a container and fluorescence labeling of at least one region of a nematode observing fluorescing regions of the nematodes by means of an electronic camera,
    calculating one of the object contour, the midpoint of the menatodes, at least one end point of the nematodes and the center of gravity of each fluorescence-labeled region of a nematode,
    delivering coordinates resulting from said step of calculating to a controller of a scanner, and
    leading laser beam, to a first selected region of a nematode by means of the scanner based on the coordinates delivered to the controller, then to a second selected region.

20. A method according to claim 19, characterized in that the laser beam is not emitted, by opening a shutter, until the beam path of the laser beam has been pointed at a selected region of the nematodes.

21. A method according to claim 19, characterized in that the beam path of the laser beam is first pointed at a reference position and then at said first and second selected regions of the nematode one after another.

22. A method according to claim 19, characterized in that the beam path of the laser beam is pointed at a reference position before each pointing at a selected region of a nematode.

23. A method according to claim 21, characterized in that the reference position is the image center of an image field observed by an electronic camera.

24. A method according to claim 19, characterized in that coordinates delivered to the scanner controller are vector coordinates.

* * * * *